(12) United States Patent
Jacobs et al.

(10) Patent No.: US 6,325,972 B1
(45) Date of Patent: Dec. 4, 2001

(54) APPARATUS AND PROCESS FOR CONCENTRATING A LIQUID STERILANT AND STERILIZING ARTICLES THEREWITH

(75) Inventors: Paul Jacobs, Canyon; Suz-Min Lin, Laguna Hills; Jenn-Hann Wang, Mission Viejo, all of CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/223,479

(22) Filed: Dec. 30, 1998

(51) Int. Cl.⁷ ........................................................ A61L 2/20
(52) U.S. Cl. ................. 422/33; 422/23; 422/27; 422/28
(58) Field of Search ................................ 422/27, 28, 23, 422/33

(56) References Cited

U.S. PATENT DOCUMENTS

| | | | |
|---|---|---|---|
| 4,169,123 | 9/1979 | Moore et al. | 422/29 |
| 4,169,124 | 9/1979 | Forstrom et al. | 422/33 |
| 4,643,876 | 2/1987 | Jacobs et al. | 422/23 |
| 4,744,951 | 5/1988 | Cummings et al. | 422/28 |
| 4,817,800 | 4/1989 | Williams et al. | 206/484 |
| 4,899,519 | 2/1990 | Williams et al. . | |
| 4,943,414 | 7/1990 | Jacobs et al. | 422/28 |
| 4,952,370 | 8/1990 | Cummings et al. | 422/28 |
| 5,492,672 | 2/1996 | Childers et al. | 422/28 |
| 5,656,238 | 8/1997 | Spencer et al. | 422/23 |
| 5,851,485 | 12/1998 | Lin et al. | 422/33 |
| 5,980,825 | 11/1999 | Addy et al. | 422/33 |
| 6,030,579 | 2/2000 | Addy et al. | 422/28 |

FOREIGN PATENT DOCUMENTS 916937   5/1999   (EP) .

OTHER PUBLICATIONS

PCT International Search Report International Application No. PCT/US99/31100 dated Mar. 30, 2000.

*Primary Examiner*—Elizabeth McKane
(74) *Attorney, Agent, or Firm*—Andrew C. Farmer (57) ABSTRACT

A method for sterilizing a device, includes the following steps: contacting the device with liquid sterilant outside or inside a sterilization chamber at a first pressure, placing the device in the chamber before or after the contacting step, and decreasing the pressure of the chamber to a second pressure below the vapor pressure of the liquid sterilant. At least the decrease in pressure below about the vapor pressure of the liquid sterilant occurs at a pumpdown rate of less than 0.8 liters per second, calculated based on the time required to evacuate the chamber from atmospheric pressure to 20 torr when the chamber is empty and dry.

21 Claims, 8 Drawing Sheets

APPARATUS AND PROCESS FOR CONCENTRATING A LIQUID STERILANT AND STERILIZING ARTICLES THEREWITH

FIELD OF THE INVENTION

The present invention relates to a process for sterilization of medical instruments using a liquid sterilant. More particularly, the invention relates to a process in which sterilization is achieved by concentrating a liquid sterilant such as hydrogen peroxide solution inside of a sterilization chamber and sterilizing articles therewith.

BACKGROUND OF THE INVENTION

Medical instruments have traditionally been sterilized using either heat, such as is provided by steam, or a chemical, such as formaldehyde or ethylene oxide in the gas or vapor state. Each of these methods has its drawbacks. Many medical devices such as fiberoptic devices, endoscopes, power tools, etc., are sensitive to heat, moisture or both. Formaldehyde and ethylene oxide are both toxic gases that pose a potential hazard to healthcare workers. Problems with ethylene oxide are particularly severe, because its use requires long aeration times to remove the gas from articles that have been sterilized. This lengthens the sterilization cycle time undesirably.

Sterilization using liquid hydrogen peroxide solution has been found to require high concentrations of sterilant, extended exposure time and/or elevated temperatures. However, sterilization using hydrogen peroxide vapor has been shown to have some advantages over other chemical sterilization processes (see, e.g., U.S. Pat. Nos. 4,169,123 and 4,169,124 which are incorporated herein by reference). The combination of hydrogen peroxide with a plasma provides certain additional advantages, as disclosed in U.S. Pat. No. 4,643,876 which is incorporated herein by reference. Commercially available sterilization devices, such as the STERRAD® sterilization systems sold by Advanced Sterilization Systems division of Ethicon, Inc. automate the process of injecting a solution of hydrogen peroxide into a sterilization chamber, vaporizing the solution to provide a hydrogen peroxide vapor, contacting articles to be sterilized with the vapor, and exciting the vapor into the plasma stage. The hydrogen peroxide for each sterilization cycle is shipped to the location of the sterilization system, generally by air or ground transportation. Preferably, as in the case with the STERRAD® brand systems, premeasured amounts of a hydrogen peroxide and water solution are provided in sealed enclosure, such as a capsule inside of a cassette housing which can be automatically opened by the system to reduce contact between the system user and the hydrogen peroxide solution. Such cassettes are described more fully in U.S. Pat. Nos. 4,817,800 and 4,899,519 incorporated herein by reference.

The sterilization of articles containing diffusion-restricted areas, such as long narrow lumens, presents a special challenge. Methods that use hydrogen peroxide vapor that has been generated from an aqueous solution of hydrogen peroxide have certain disadvantages. One disadvantage is that because water has a higher vapor pressure than hydrogen peroxide, it will vaporize faster. Another disadvantage is that because of its lower molecular weight, water will diffuse faster than hydrogen peroxide in the vapor state. Because of these physical properties, when an aqueous solution of hydrogen peroxide is vaporized in the area surrounding the items to be sterilized, the water reaches the items first and in higher concentration. The water vapor inhibits penetration of hydrogen peroxide vapor into diffusion-restricted areas, such as small crevices and long narrow lumens. Simply employing a more concentrated solution of hydrogen peroxide fails to adequately address the problem due to the difficulty in handling highly concentrated hydrogen peroxide solutions. Transportation of such solutions can be particularly difficult. In general, such solutions are limited to concentrations of less than 60% hydrogen peroxide, however, regulations and the like regarding such concentrations may of course be modified in the future. In any event, shipping and handling of highly concentrated solutions remains impractical.

U.S. Pat. No. 4,952,370 discloses a sterilization process in which aqueous hydrogen peroxide vapor is first condensed on the article to be sterilized, followed by application of a vacuum to the sterilization chamber to remove the water and hydrogen peroxide from the article. This method is suitable for surface sterilization, but not for sterilization of diffusion-restricted areas such as long narrow lumens because it depends on the diffusion of hydrogen peroxide vapor into the lumen to effect sterilization.

U.S. Pat. No. 4,943,414 discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the existing pressure differential, increasing the sterilization rate for lumens, but has the disadvantage that the vessel needs to be attached to each lumen to be sterilized. In addition, water is vaporized faster and precedes the hydrogen peroxide vapor into the lumen.

In U.S. Pat. No. 5,492,672, there is disclosed a process for sterilizing narrow lumens. This process uses a multicomponent sterilant vapor and requires successive alternating periods of flow of sterilant vapor and discontinuance of such flow. A complex apparatus is used to accomplish the method. Because flow through of vapor is used, closed end lumens are not readily sterilized in the process.

U.S. Pat. No. 4,744,951 to Cummings attempts to address this problem by providing a separate prechamber connected to the sterilization chamber. Hydrogen peroxide is first admitted to the prechamber where it is concentrated in a distillation procedure employing the differing vapor pressures of hydrogen peroxide and water. Water's higher vapor pressure allows one to select a vaporization pressure which selectively vaporizes water from a hydrogen peroxide solution, thus concentrating the solution. Cummings pumps air out of the prechamber and lowers its pressure to a level at which the water preferentially vaporizes from the hydrogen peroxide solution. The pump which is evacuating the prechamber draws out the water vapor thus released from solution to concentrate the remaining solution. To prevent the water vapor from traveling into the narrow spaces such as endoscope lumens, Cummings carries out the concentration process in the prechamber. This adds complexity be requiring additional chambers, pumps and valves.

Those of skill in the art, both in Cummings day, and now, would not think to employ such a concentration process in the same chamber as the sterilization occurs due to the problem of water vapor rushing to occlude the narrow lumens. In fact, the theory predicts that such a process would sterilize lumens less well than by simply vaporizing all of the hydrogen peroxide solution at once, because the slow vaporization would more efficiently block the lumen with water vapor. However, the present inventors have suprisingly found that concentrating the hydrogen peroxide vapor within the sterilization chamber greatly increases the ability to sterilize long narrow lumens over the convential process of essentially vaporizing all of the hydrogen peroxide at once.

SUMMARY OF THE INVENTION

DETAILED DESCRIPTION OF THE PREFERRED EMBODIMENTS

Sterilizing the inside of lumened devices has always posed a challenge to sterilization systems. Copending U.S. application Ser. No. 08/628,965, now U.S. Pat. No. 6,030,579, the entire contents of which are hereby incorporated by reference, discloses a method of hydrogen peroxide vapor sterilization of diffusion-restricted environments, such as long narrow lumens, at pressures less than the vapor pressure of hydrogen peroxide by pretreating the article to be sterilized with a dilute solution of hydrogen peroxide prior to exposure to a vacuum. U.S. Pat. No. 5,851,485, incorporated herein by reference, controls the pumpdown rate.

Figure 1:
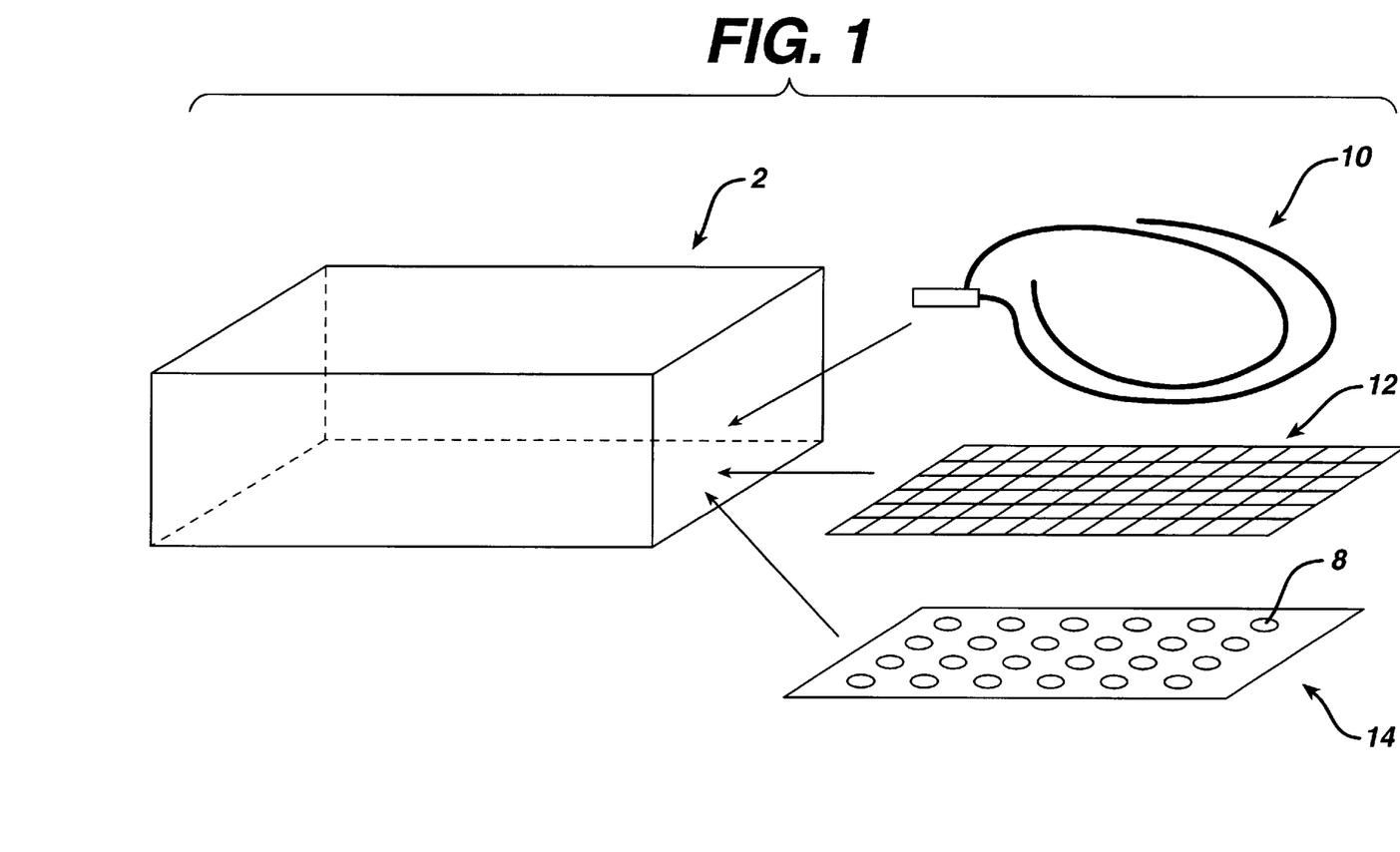
FIG. 1 is a schematic diagram of a chamber and accessories suitable for use in the hydrogen peroxide sterilization process of the invention.
Figure 2:
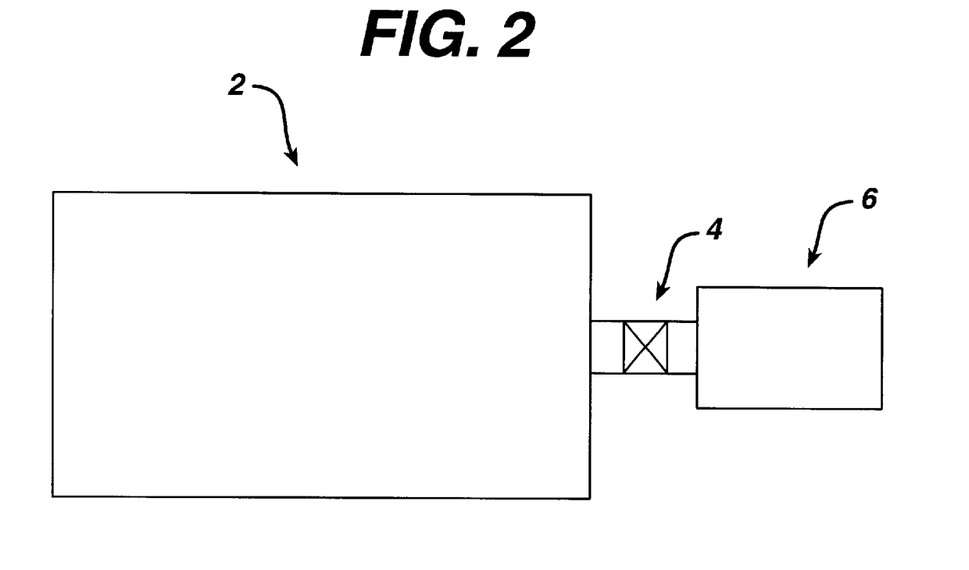
FIG. 2 is a schematic diagram of a chamber, pump and throttle valve for use in the hydrogen peroxide sterilization process of the invention.

An apparatus useful in the process of the present invention is shown schematically in FIGS. 1 and 2 and comprises a chamber 2, a throttle valve 4 and a pump 6. In FIG. 2, the chamber 2 is attached to the pump 6 by the throttle valve 4. The valve 4 can be controlled either automatically or manually to maintain the pressure. In the automatic mode of operation, the throttle valve 4 opens based on the pressure in the chamber via a pressure transducer and valve controller. Such valves are commercially available from, for example, MKS (Andover, Md.).

Hydrogen peroxide can be introduced into the system in any fashion. In one emobdiment, a dilute, aqueous solution of hydrogen peroxide is placed in wells 8 as shown in FIG. 1. The aqueous solution of hydrogen peroxide can also be placed within the lumen of long narrow objects to be sterilized. As the pressure in the sterilization chamber 2 is reduced, the hydrogen peroxide vaporizes and contacts the surface to be sterilized (i.e., colonoscope 10 in FIG. 1) which is placed on metal grid 12 which rests on tray 14. In a preferred embodiment, the tray can be configured with a plurality of wells designed to retain a known volume of liquid sterilant. In one embodiment, the volume of sterilization chamber 2 is about 18.5 liters and its dimensions are about 22" (55.9 cm)×4.25" (10.8 cm)×12" (30.5 cm).

Figure 3:
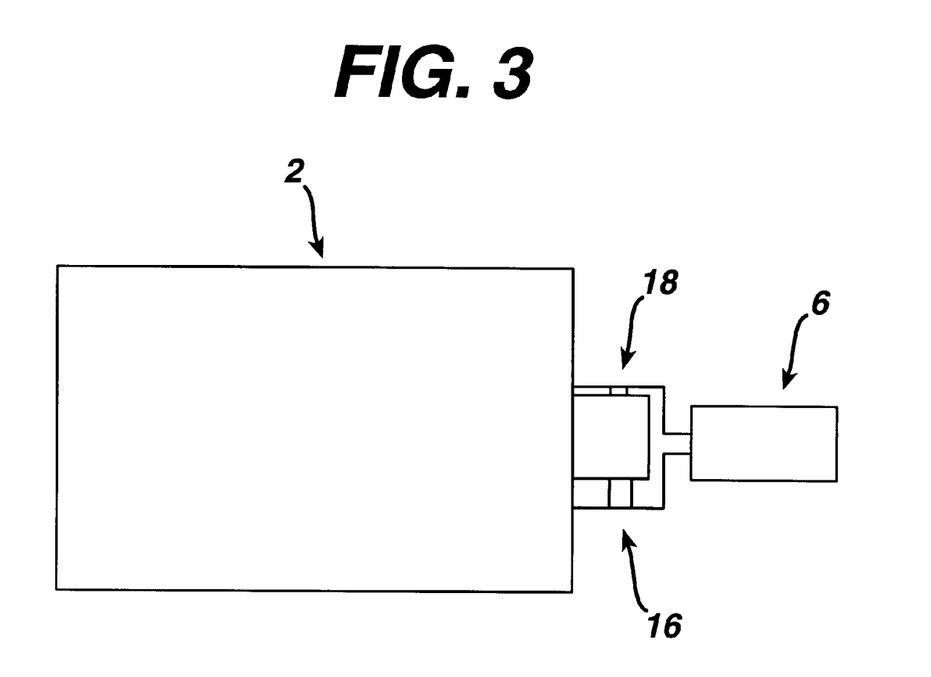
FIG. 3 is a schematic diagram of a system with one pump and two valves, one valve having a larger pump vacuum line for quicker pumpdown and one having a smaller vacuum line for slower pumpdown.

FIG. 3 illustrates a parallel two-valve arrangement for use in the sterilization process of the invention. In this embodiment, the chamber 2 is in fluid communication with the pump 6 via valves 16 and 18. Valve 16 mediates the initial rapid evacuation, the first step of two step evacuation process. Valve 18 mediates slow evacuation, the second step of the process, which ensures maximal contact of the article to be sterilized with the vaporized aqueous hydrogen peroxide. The pumpdown rate can be controlled by the pumping speed and/or the percent opening of the valve. Either valve can be used to maintain the pressure. In practice, controlling the process so that all of the water evaporates before any of the hydrogen peroxide evaporates is very difficult, yet the preferential evaporation and elimination of water vapor from the system effectively concentrates the hydrogen peroxide therein without the attendant complexity of shipping and handling concentrated hydrogen peroxide solutions prior to vaporization.

As the water evaporates from solution its voume greatly increases thus raising the pressure in the system and requiring additional pumping to extract the water vapor to maintain the pressure between the two vapor pressures. Also, the vapor pressures change with changing conditions within the chamber.

Figure 4:
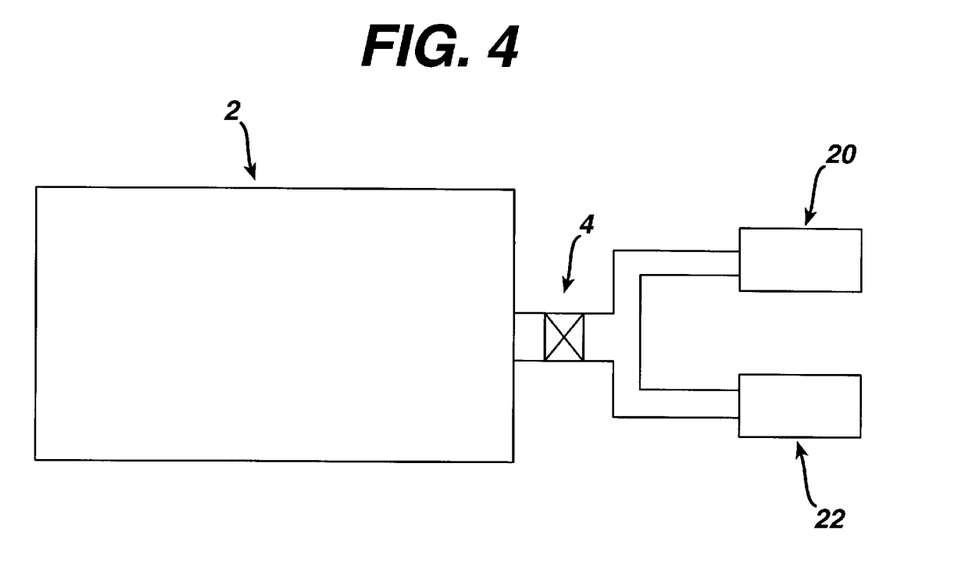
FIG. 4 is a schematic diagram of a single valve sterilization system having two pumps, one for slower pumpdown and one for quicker pumpdown.
Figure 5:
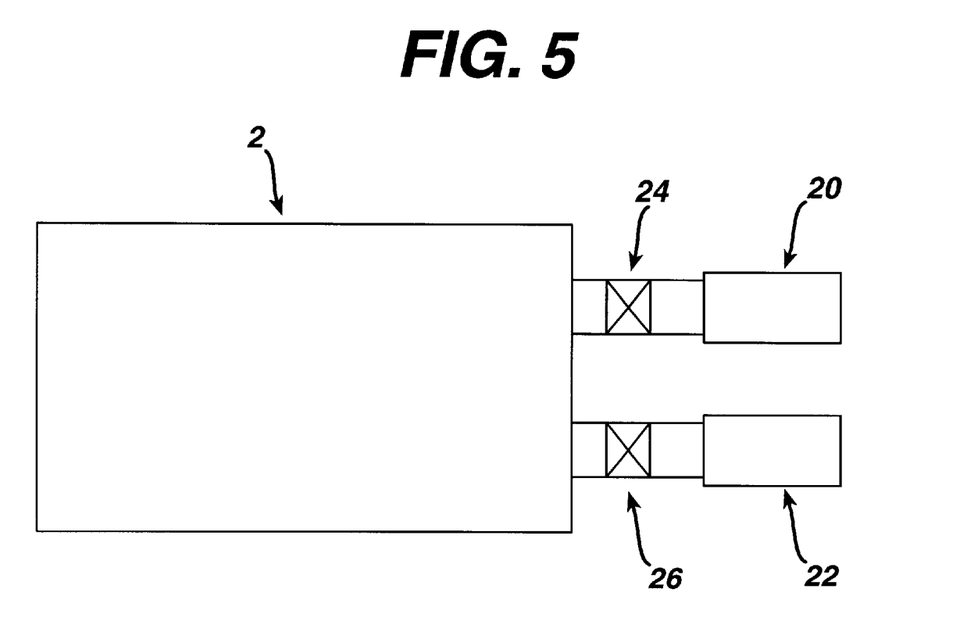
FIG. 5 is a schematic diagram of a system with two pumps and two valves, one pump for slower pumpdown and one for quicker pumpdown.

FIG. 4 illustrates a sterilization apparatus having two pumps 20 and 22, and one valve 4. Pump 20 allows quicker pumpdown of the chamber 2, while pump 22 allows slower pumpdown. FIG. 5 illustrates an alternate configuration having two valves 24 and 26 in fluid communication with the pumps 20 and 22, respectively.

Regardless of which configuration is used, hydrogen peroxide can be introduced into the chamber as a liquid. In one preferred embodiment, hydrogen peroxide is introduced as a vapor and the chamber parameters are changed so that the vapor condenses as a liquid on the surface of interior of an article to be sterilized. Such changes include increasing the pressure.

The aqueous solutions of hydrogen peroxide can be relatively dilute, e.g. as low as 1–6% peroxide by weight, since sterilization is not achieved through contact with the hydrogen peroxide solution, but rather is achieved at low temperatures (preferably 15°–80° C. more preferably 20°–60° C. still more preferably 40°–55° C.) and in short periods of time (preferably less than one hour, and more preferably less than one-half hour) upon exposure to hydrogen peroxide under vacuum. The method of the present invention is particularly effective with articles having inaccessible or hard-to-reach places. Such articles include long, narrow lumens, hinges and other articles having spaces where diffusion of vapors is restricted. Although hydrogen peroxide is used in the examples described herein, the use of other liquid sterilants which have vapor pressures lower than the vapor pressure of the solvent in which they are provided are also contemplated. Such sterilants include, for example, aqueous peracetic acid solution and aqueous glutaraldehyde solution.

Preferably, the article to be sterilized is contacted with sterilant prior to the vaporization step to localize at least some of the vaporization in the diffusion restricted areas. Such contacting can be accomplished either directly or indirectly. Direct contacting includes methods such as static soaking, flow through, aerosol spray, condensation of a vapor. Any other methods involving physically contacting the articles to be sterilized with sterilant would be considered direct contacting. Indirect contacting includes those methods in which sterilant is introduced into the chamber, but not directly on or in the articles to be sterilized.

At the end of the process, deep vacuum can be used to remove residual sterilant. A plasma can also be used to both enhance sterilization efficacy and to remove residual sterilant.

The pumps shown schematically in the figures can be any commercially available pump. Two preferred pumps are from Leybold Vacuum Products, Inc. (Export, Pa.) (Model D16A, pump rate =400 liters/min) and KNF Neuberger, Inc. (Trenton, N.J., Model N740, pump rate =45 liters/min). The Leybold pump can reach a pressure of less than 0.1 torr and the KNF pump can reach a pressure of less than 10 torr.

For certain substrates being sterilized, such as nylon or polyurethane, excess hydrogen peroxide in the system may leave a residual which is difficult to remove. In order to avoid an excess residual, the vapor concentration of hydrogen peroxide is preferably kept below 30 ml/l, more preferably less than 20 mg/l, and more preferably still less than 15 mg/l. If higher vapor concentrations of hydrogen peroxide are desired, excess residual can be removed using a gas plasma. When using substrates such as stainless steel, polyethylene or polypropylene, which do not retain a residual, there is no reason to limit to the amount of peroxide which can be present in the vapor phase in the system during sterilization.

To further reduce water within the system, the chamber 2 may be dried prior to the introduction of hydrogen peroxide. Many means may be employed to drive water out of the chamber. Primarily, this is accomplished by vaporizing the water and pumping it out of the chamber. The vaporization can be accomplished with heat, plasma induction, vacuum or the like either alone or in combination. Merely drawing a vacuum prior to introducing the hydrogen peroxide accomplishes a benficial drying of the chamber 2. If the chamber 2 is heated during this process and if a high energy electromagnetic field is applied to urge the water into the plasma stage the drying is enhanced. U.S. Pat. No. 5,656,238 issued on Aug. 12, 1997 to Spencer at al. and incorporated herein by reference teaches such techniques in more detail.

Figure 6:
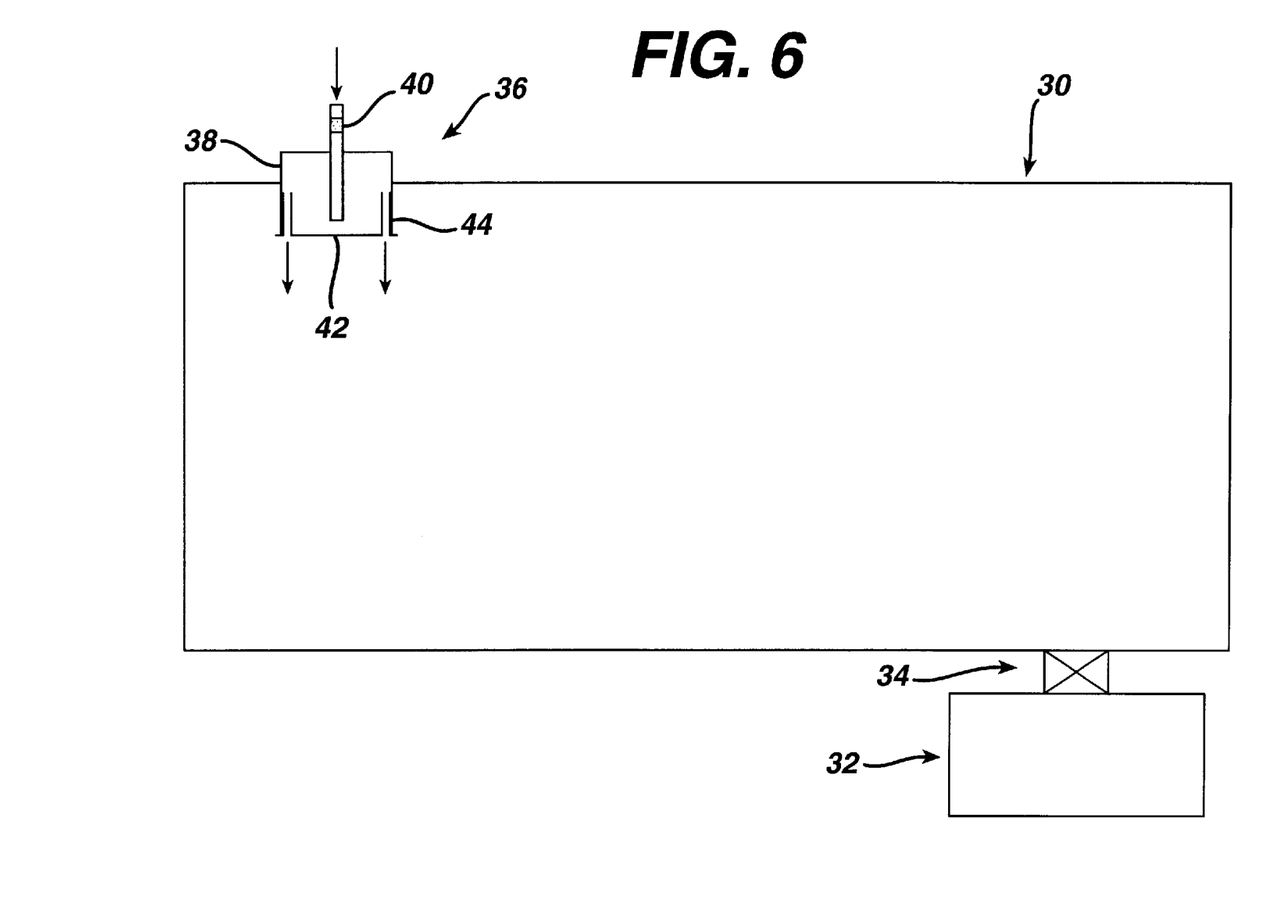
FIG. 6 is a schematic diagram of a system with a vaporizer.
Figure 7:
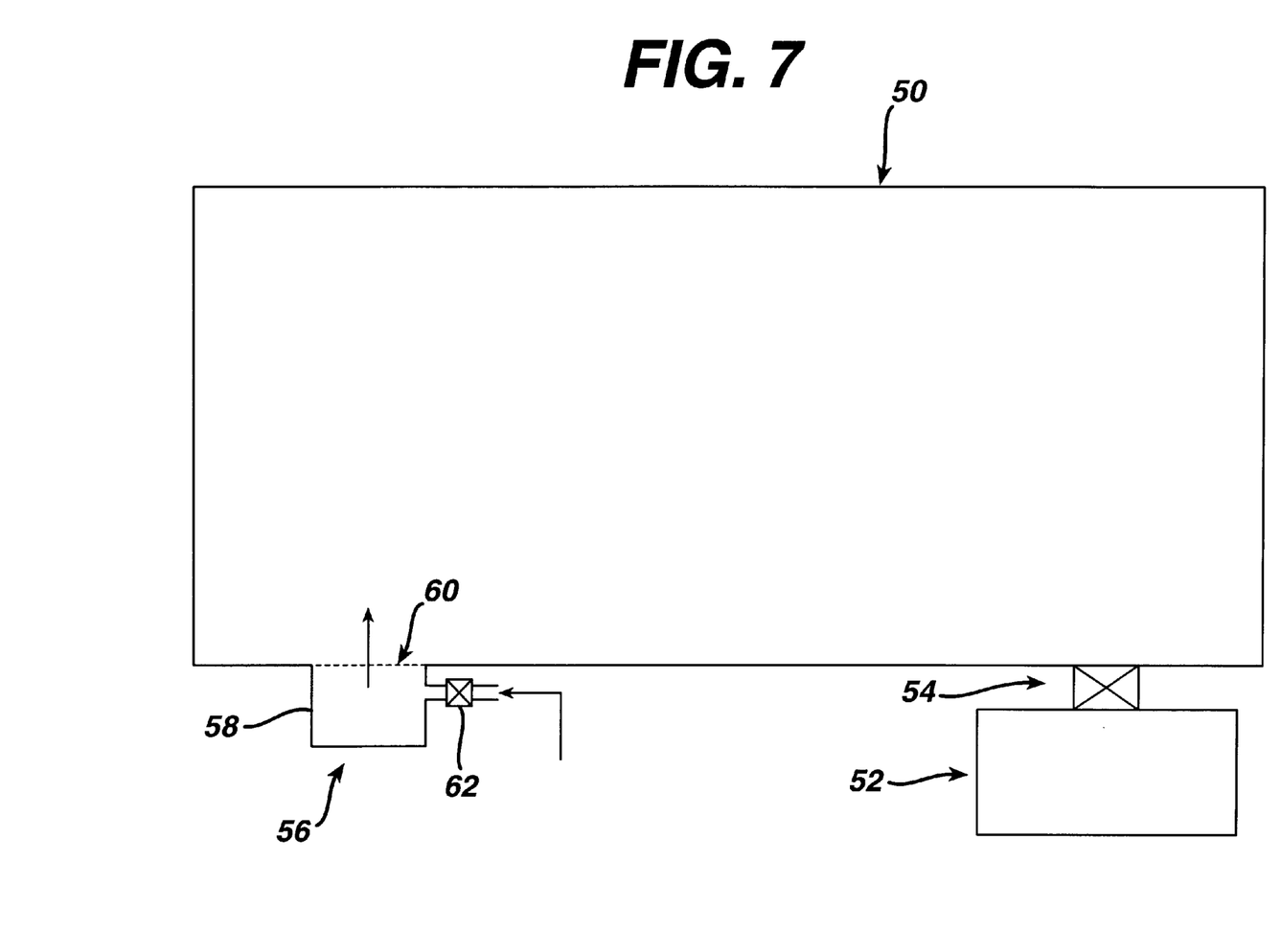
FIG. 7 is a schematic diagram of a system with an alternative vaporizer.
Figure 8:
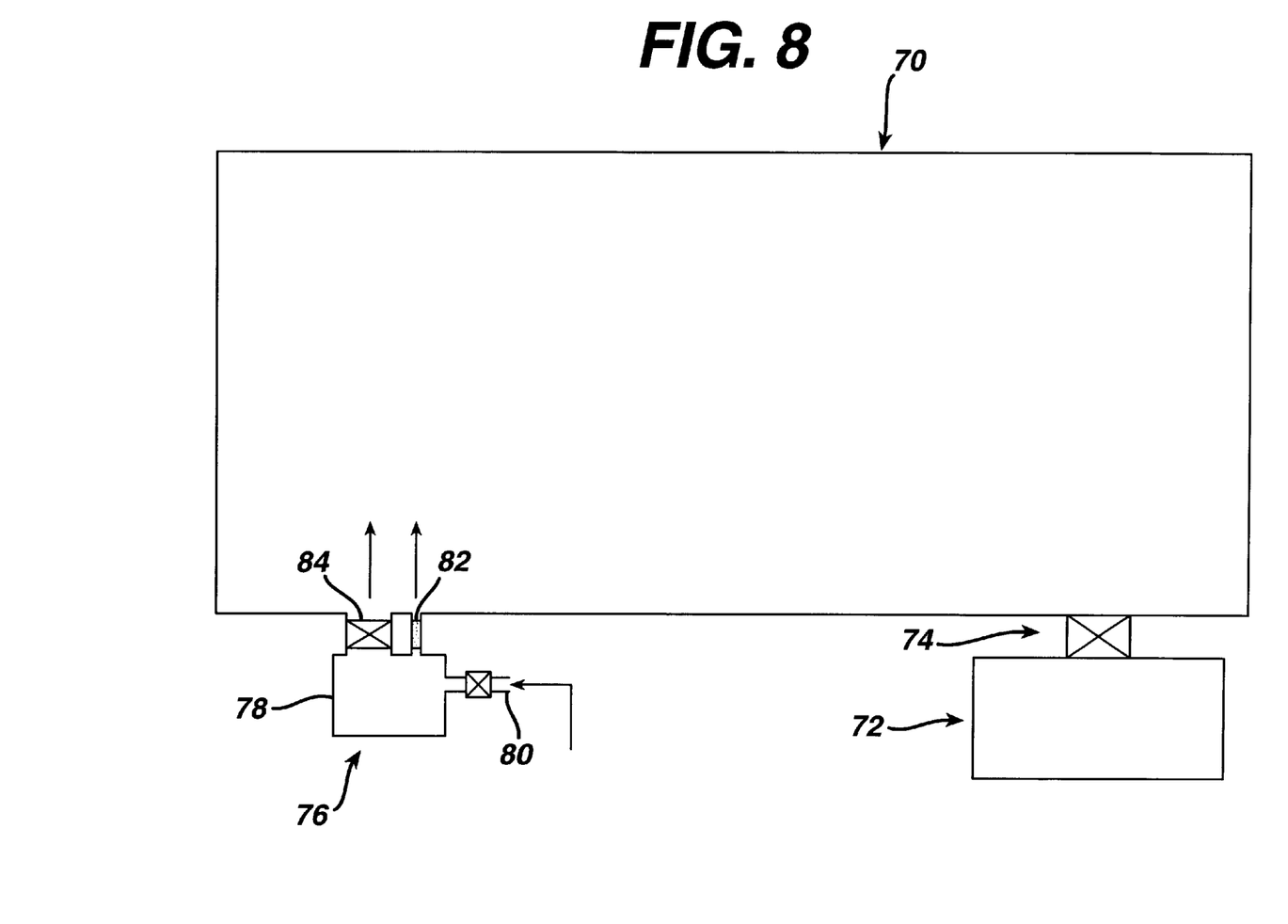
FIG. 8 is a schematic diagram of a system with a further alternative vaporizer.

Vaporization of the hydrogen peroxide can be achieved using well known methods as described above; FIGS. 6 to 8 show several new preferred methods. In FIG. 6, a chamber 30 is evacuated by a pump 32 separated from the chamber 30 by a throttle valve 34. A vaporizer 36 comprises a housing 38 in fluid communication with the chamber 30 and into which extends a liquid feeding nozzle 40 from outside of the chamber 32. A cup 42 within the housing 38 receives hydrogen peroxide from the nozzle 40. The hydrogen peroxide can be vaporized as it exits the nozzle 40, or more preferably in a controlled fashion from the cup 42 by controlling the temperature of the cup 42 and the pressure in the chamber 30. Temperature control of the cup 42 can be as simple as thermally isolating it from the chamber 30, or a more active control system can be employed such a cooling coil or the like to maintain the cup 42 at a desired low temperature. Preferably, the entire vaporizer 36 is thermally isolated from the chamber 30 or temperature controlled in some fashion. Lower temperatures of vaporization enhance the preferential vaporization of water by exploiting the larger difference between the vapor pressures of water and hydrogen peroxide at lower temperatures. Creating a diffusion restriction 44 between the vaporizer 36 and chamber 30 enhances the preferential extraction of water vapor from the chamber as water vapor will more easily traverse the diffusion restriction and be pumped out of the chamber during the vaporization process. The diffusion restriction 44 may be simply reducing the clearance between the cup 42 and housing 38 through with the vapor must travel to reach the chamber 30.

FIG. 7 shows a similar chamber 50, pump 52 and valve 54 with modified vaporizer 56. The vaporizer 56 comprises a chamber 58 separated from the chamber 50 by a diffusion restriction 60, such as a permeable membrane. Liquid hydrogen peroxide solution enters the chamber 58 through a valve 62. FIG. 8 illustrates a similar arrangement with a chamber 70, pump 72, valve 74, and vaporizer 76 with a chamber 78 and valved hydrogen peroxide solution inlet 80. Restriction of the diffusion between the vaporizer chamber 78 and main chamber 70 is variable. During initial vaporization when primarily water is vaporizing the vapors pass through a tight diffusion restriction 82. After the concentration of the hydrogen peroxide solution reaches a given level a valve 84 may be opened to speed the vaporization and diffusion of the concentrated hydrogen peroxide solution.

Preferably, the temperature in the chamber is no less than 5° C. nor more than 150° C. with the range of 50 to 65° C. being preferred, and the pressure should be no less than 0.01 torr, nor typically greater than atmosphere during the process, with the lowest vacuum being typically 0.4 torr and the diffusion pressure preferably being between 2 and 10 torr, although other conditions within the spirit of the invention will be apparent to those of skill in the art. During the concentration stage, the pressure should not fall below 0.5 torr. Shorter overall cycles are preferred for convenience, with 5 minutes being a desirable goal, but longer times upwards of 6 hours or more may be warranted in some circumstances.

Tables 1 and 2 illustrate the effectiveness of the present invention. The experiments were run on a chamber of 73 liters at 45° C. with 1780 mg of hydrogen peroxide 59% solution. The diffuser is separated from the chamber by 12 2 mm diameter holes to effect diffusion restriction.

TABLE 1

| | Test conditions | | | | |
| --- | --- | --- | --- | --- | --- |
| | Normal process | | New process | | |
| Step | Test A | Test B | Test C | Test D | Test E |
| 1 | Open valve | Open valve | Open valve | Open valve | Open valve |
| 2 | Vacuum to 0.3 torr | Inject H$_2$O$_2$ at 1 atm | Vacuum to 30 torr | Vacuum to 0.3 torr | Vacuum to 0.3 torr |

TABLE 1-continued

| | Test conditions | | | | |
|---|---|---|---|---|---|
| | Normal process | New process | | | |
| Step | Test A | Test B | Test C | Test D | Test E |
| 3 | Close valve | Vaporization & diffusion | Inject $H_2O_2$ at 30 torr | Inject $H_2O_2$ at 0.3 torr | Close valve |
| 4 | Inject $H_2O_2$ at 0.3 torr | Vacuum to about 2 torr | Vaporization & diffusion | Vaporization & diffusion | Inject $H_2O_2$ at 0.3 torr |
| 5 | Vaporization & diffusion | Close valve | Vacuum to about 2 torr | Vacuum to about 2 torr | Vaporization & diffusion |
| 6 | Vent to 1 atm | Vaporization & diffusion | Close valve | Close valve | Open valve |
| 7 | | Vent to 1 atm | Vaporization & diffusion | Vaporization & diffusion | Vacuum to about 2 torr |
| 8 | | | Vent to 1 atm | Vent to 1 atm | Close valve Vaporization & diffusion |
| 9 | | | | | Vent to 1 atm |

TABLE 2

| | Sterility test results (positives/samples) | | | | |
|---|---|---|---|---|---|
| | Normal process | New process | | | |
| Lumen size | Test A | Test B | Test C | Test D | Test E |
| 1 × 400 mm | 2/2 | 0/2 | 0/2 | 0/2 | 0/2 |
| 1 × 350 mm | 2/2 | 0/2 | 0/2 | 0/2 | 0/2 |
| 1 × 300 mm | 2/2 | 0/2 | 0/2 | 0/2 | 0/2 |
| 1 × 250 mm | 2/2 | 0/2 | 0/2 | 0/2 | 0/2 |

Monitoring of the temperature, pressure and hydrogen peroxide conditions within the chamber 30 (FIG. 6) allows the process to be controlled more precisely. Preferably, an automated control system, preferably employing a computer processor, recieves inputs of the temperature, pressure and perhaps also the hydrogen peroxide concentration and calculates the optimal pressure at which to maintain the chamber to remove the water from the hydrogen peroxide solution and from the chamber 30. It can also determine when the solution is sufficiently concentrated. For instance, it may be desired to only concentrate the solution to a certain degree so as to minimize the loss of hydrogen peroxide from the chamber, thereby minimizing hydrogen peroxide emissions from the chamber. While preferentially vaporizing the water from the solution, some hydrogen peroxide will also vaporize. Accordingly, one may wish to balance the efficient use of the quantity of hydrogen peroxide within the solution against the goal of eliminating all water from the solution and the chamber. By monitoring the ratio of water and peroxide the vapor phase, the valve 34 can be controlled to remove the vapor until the desired ratio is achieved. The ratio can be determined using a hydrogen peroxide monitor and a moisture monitor, or by using a hydrogen peroxide monitor and a pressure sensor and then calculating the water using the PVRT equation and making the assumption that water and peroxide are essentially the only gases within the chamber 34.

It is known that certain spectra of light passing through the chamber can be measured to determine the hydrogen peroxide concentration. One particular method is disclosed in co-pending U.S. application Ser. No. 08/970,925 filed Nov. 14, 1997, incorporated herein by reference.

Table 3 illustrates the effects of the ratio of hydrogen peroxide vapor to water vapor in the chamber 30 on the ability to sterilize long narrow lumens or other diffusion restricted environments. Water vapor was first introduced into the system and then essentially pure hydrogen peroxide vapor was introduced by liberation from a solid form. The lower concentrations of water show no failures, whereas with the higher ratio in the last column the efficacy decreased and in one test 3 out of 3 samples failed. Table 4 shows similar results by comparing a sterilization process in which the concentration of hydrogen peroxide is not increased according to the present invention with a process in which it is increased. Table 5 shows the degree of concentration achieved according to the present invention. By monitoring the concentration (i.e. the ratio of hydrogen peroxide to water) during the sterilization cycle it should be possible to achieve the long sought goal of parametric release. One could be assured that if the proper concentration was maintained for a sufficient period of time that a particular load of instruments placed within the chamber 30 and sterilized according to the present invention then the process would be sufficiently predictable so as to allow the load to be released for use without further checking with a biological indicator. Typically, such processes always employ a biological indicator in the load, such as with a test load of microorganisms, which is then checked to ensure that sufficient sterilization has been achieved to kill all of the test microorganisms. With parametric release the time consuming process of biological indicators can be skipped.

TABLE 3

(A) Effect of water to peroxide ratio on efficacy
Efficacy with *Bacillus subtilis* var.
niger on SS blade in 3 mm × 500 mm SS LTU in 173L chamber

| | Sterility results (positives/samples) | | |
|---|---|---|---|
| Diffusion time (minutes) | 0.653 mg/L $H_2O$ 6 mg/L $H_2O_2$ | 3.266 mg/L $H_2O$ 6 mg/L $H_2O_2$ | 6.532 mg/L $H_2O$ 6 mg/L $H_2O_2$ |
| 5 | 0/3 | 0/3 | 3/3 |
| 10 | 0/3 | 0/3 | 2/3 |
| 15 | 0/3 | 0/3 | 0/3 |
| 30 | 0/3 | 0/3 | 0/3 |

TABLE 5

(A) Concentrating the 59% peroxide solution

| | Ratio of peroxide to water | | |
|---|---|---|---|
| | Before concentrating | Right after concentrating | After all peroxide vaporized |
| Solution in vaporizer | 1.4:1 | 19:1 | none |
| Vapor in chamber | <1.4:1 | 0.85:1 | 4.9:1 |

TABLE 4

(A) Effect of water to peroxide ratio on efficacy

| | Sterility results (positives/samples) | |
|---|---|---|
| Lumen Dimension (Diameter) × (length) | Without concentrating process 8.43 mg/L $H_2O$ 12 mg/L $H_2O_2$ | With concentrating process 1.49 mg/L $H_2O$ 7.3 mg/L $H_2O_2$ |
| 1 × 400 mm | 2/2 | 0/2 |
| 1 × 350 mm | 2/2 | 0/2 |
| 1 × 300 mm | 2/2 | 0/2 |
| 1 × 250 mm | 2/2 | 0/2 |

The process may be further enhanced by admitting sufficient hydrogen peroxide into the system so as to force some of the vaporized solution to condense upon the instruments being sterilized within the system. As described above, the solution can be vaporized by admitting it into the system at any pressure above the vapor pressures of water and hydrogen peroxide in the solution and then vaporized by reducing the pressure, or by admitting the solution at a pressure substantially below these vapor pressures whereupon it will start to vaporize thus releasing gas and increasing the pressure. In the second scenario if the pressure is then further reduced by pumping the concentration of the hydrogen peroxide in the system can be increased. This is especially true if the pressure rises to a level at least above the vapor pressure of hydrogen peroxide thereby limiting further vaporization of hydrogen peroxide from solution and perhaps encouraging some of the hydrogen peroxide to condense upon objects such as instruments within the system. Some of the water vapor would likely also condense in such event. By controlling the pressure excess water vapor would be exhausted from the system and then the condensed solution would re-vaporize. To the extent that such solution had condensed within diffusion restricted areas the re-vaporization therein would further increase the concentration in the those areas to enhance the sterilization efficacy therein. The quantity of solution admitted will primarily determine the pressure rise to initiate such condensaation. The process is described in more detail in our co-pending application entitled "Sterilization of Diffusion-Restricted Area by Re-Vaporizing the Condensed Vapor" filed contemporaneously herewith.

A typical cycle might comprise placing a load of instruments (not shown) within a CSR wrapped tray within the chamber 30 and then drawing a vacuum on the chamber 30 with the pump 32 down to below 1 torr or about 0.4 torr. An electromagnetic field applied to the chamber 30 at such time tends to drive any remaining water into the vapor or plasma stage so that it can be removed by the pump 32. The pump 32 can be cycled or merely run continuously with the valve 34 controlling the vacuum process. Fresh dry air may be admitted to the chamber 30 including raising of the pressure back to atmosphere. Preferably the hydrogen peroxide solution, preferably a 59% hydrogen peroxide solution, is admitted to the vaporizer 36 at atmospheric pressure and then the pump 32 exhausts the chamber 30 to a level at which the solution begins to vaporize. A monitor 100 for hydrogen peroxide vapor and monitor 102 (see FIG. 6) for water vapor in connection with an automated control system 104 can be employed to optimize the pressure conditions to enhance the initial vaporization and exhaust of water vapor. After the solution is sufficiently concentrated the pressure in the chamber 30 can be further lowered to vaporize the remaining solution. The valve 32 is closed to isolate the chamber 30 and the vaporized hydrogen peroxide solution is allowed to diffuse throughout the chamber to contact the instruments. Additional dry air or other gas can be admitted at this time to help push the sterizing vapors into diffusion restricted areas, with the chamber 30 then further exhausted to resume a vacuum in the range of 2 to 10 torr. Additional admissions of air and vacuum can be employed, especially in connection with additional admission and concentration of hydrogen peroxide solutions. After the hydrogen peroxide vapors have diffused throughout the chamber for a sufficient time aan electromagnetic field may be applied to drive the vapor into the plasma stage and effect further steilization. When the field is removed the ions formed from the hydrogen peroxide recombine as water and oxygen, leaving little residual hydrogen peroxide. The chamber can be raised to atmospheric pressure and the load removed.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method of furnishing concentrated hydrogen peroxide vapor to an article comprising the steps of:

placing the article into a chamber containing an inner atmosphere;

placing a solution comprising hydrogen peroxide and water into fluid communication with the chamber, said solution having a ratio of hydrogen peroxide to water;

vaporizing the solution in the inner atmosphere to form water vapor and hydrogen peroxide vapor;

selectively drawing water vapor from the chamber to increase a ratio of hydrogen peroxide to water in the chamber;

contacting the article with the hydrogen peroxide vapor; and wherein the step of contacting the article with the hydrogen peroxide vapor is limited to less than one hour and achieves a level of sterilization such that in a straight round lumen having two open ends, a diameter of 1 mm and a length of 250 mm with $10^6$ viable spores of *B. Stearothermophilus* located within the lumen at a midpoint thereof, all of the spores would be killed.

2. A method according to claim 1 wherein the ratio of hydrogen peroxide vapor to water vapor after the step of selectively drawing water vapor from the chamber exceeds the ratio of hydrogen peroxide to water in said solution.

3. A method according to claim 1 wherein the ratio of hydrogen peroxide to water, by weight, after the step of selectively drawing water vapor from the chamber exceeds 3 to 1.

4. A method according to claim 3 wherein the ratio of hydrogen peroxide to water in said solution, by weight, is less than 3 to 1.

5. A method according to claim 3 wherein the ratio of hydrogen peroxide to water in said solution, by weight, is less than 3.2

6. A method according to claim 3 wherein the ratio of hydrogen peroxide to water, by weight, after the step of selectively drawing water vapor from the chamber exceeds 4 to 1.

7. A method according to claim 1 wherein the step of selectively drawing water vapor from the chamber comprises placing said solution within a diffusion restricted environment in fluid communication with the chamber during the step of vaporizing the solution.

8. A method according to claim 7 wherein the diffusion restricted environment is more diffusion restricted during the step of selectively drawing water vapor from the chamber than during a portion of the step of vaporizing the solution during which the hydrogen peroxide is vaporizing at a faster rate than the water.

9. A method according to claim 7 wherein the water vapor is drawn from the chamber through one or more exhaust ports and wherein the one or more exhaust ports are physically remote from the diffusion restriction.

10. A method according to claim 1 wherein the step of selectively drawing water vapor from the chamber comprises the steps of controlling the temperature and pressure of the solution during the step of vaporizing the solution to enhance vaporization of the water from solution versus vaporization of hydrogen peroxide and extracting at least a portion of the water vapor from the chamber.

11. A method according to claim 10 wherein the temperature of the atmosphere in the chamber is above room temperature and the temperature of the solution during the vaporizing step is at least 10° C. below the temperature of the atmosphere in the chamber.

12. A method according to claim 1 wherein the step of selectively drawing water vapor from the chamber comprises the steps of maintaining the solution at a pressure below the vapor pressure of the water in the solution and above the vapor pressure of the hydrogen peroxide in the solution.

13. A method according to claim 1 wherein the solution is vaporized by pumping a portion of the atmosphere out of the chamber to lower the pressure of the chamber at a rate selected to control removal of the water and hydrogen peroxide from the solution so as to concentrate the hydrogen peroxide remaining in the chamber.

14. A method according to claim 1 wherein the temperature of the solution during the vaporizing step is held below the temperature of the atmosphere in the chamber whereby to increase the vapor pressure of the water in the solution relative to the hydrogen peroxide in the solution whereby to enhance vaporization of the water from the solution in preference to vaporizing the hydrogen peroxide from the solution.

15. A method according to claim 13 wherein the solution is vaporized in a vaporizer which is in fluid communication with the chamber and wherein the vaporizer is thermally isolated from the chamber.

16. A method according to claim 1 and further comprising the steps of controlling the temperature and pressure of the solution during a least a first portion of the vaporizing step so as to selectively vaporize water from the solution and concentrate hydrogen peroxide therein to form a concentrated solution and during a second portion of the vaporizing step raising the temperature of the concentrated solution and vaporizing the concentrated solution.

17. A method a ccording to claim 1 and further comprising the steps of controlling the temperature and pressure of the solution during a least a first portion of the vaporizing step so as to selectively vaporize water from the solution and concentrate hydrogen peroxide therein to form a concentrated solution and during a second portion of the vaporizing step not withdrawing atmosphere from the chamber.

18. A method according to claim 1 and further comprising the step of drying the chamber prior to the step of vaporizing the solution.

19. A method according to claim 18 wherein the step of drying the chamber comprises pumping a portion of the atmosphere out of the chamber.

20. A method according to claim 18 wherein the step of drying the chamber comprises applying energy to excite molecules of liquid water within the chamber into the gaseous or plasma state of matter and pumping a portion of the atmosphere out of the chamber.

21. A method according to claim 1 wherein the solution comprises peracetic acid.

* * * * *